United States Patent [19]

Fahey et al.

[11] Patent Number: 4,845,066

[45] Date of Patent: Jul. 4, 1989

[54] PREPARATION OF PILLARED CLAY

[75] Inventors: Darryl R. Fahey; Keith A. Williams; Jesse R. Harris; Paul R. Stapp, all of Bartlesville, Okla.

[73] Assignee: Phillips Petroleum Company, Bartlesville, Okla.

[21] Appl. No.: 236,587

[22] Filed: Aug. 25, 1988

[51] Int. Cl.$^4$ .......................... B01J 20/10; B01J 21/16
[52] U.S. Cl. .......................................... 502/84; 502/62
[58] Field of Search ..................................... 502/62, 84

[56] References Cited

U.S. PATENT DOCUMENTS

| | | | |
|---|---|---|---|
| 3,657,151 | 4/1972 | Noble | 502/62 |
| 4,176,090 | 11/1979 | Vaughan et al. | 252/455 Z |
| 4,216,188 | 8/1980 | Shabrai et al. | 423/118 |
| 4,235,751 | 11/1980 | Del Pesco | 502/62 |
| 4,238,364 | 12/1980 | Shabtai | 252/455 R |
| 4,248,739 | 2/1981 | Vaughan et al. | 252/455 R |
| 4,271,043 | 6/1981 | Vaughan et al. | 252/455 R |
| 4,452,910 | 6/1984 | Hopkins et al. | 502/84 |
| 4,465,892 | 8/1984 | Jacobs et al. | 585/666 |
| 4,629,713 | 12/1986 | Suzuki et al. | 502/62 |
| 4,637,991 | 1/1987 | Battiste et al. | 502/68 |
| 4,742,033 | 5/1988 | Harris et al. | 502/68 |
| 4,774,212 | 9/1988 | Drezdon | 502/62 |

*Primary Examiner*—Carl F. Dees
*Attorney, Agent, or Firm*—K. K. Brandes

[57] ABSTRACT

A process for preparing a pillared interlayered clay comprises heating a smectite clay containing material with a solution comprising a polymeric cationic hydroxy metal complex of a suitable metal (preferably aluminum) and a surfactant having the formula of $R^1$—O—(CHR$^2$—CHR$^2$O)$_x$H, wherein, $R^1$ is an aliphatic $C_6H_{13}$—$C_{24}H_{49}$ hydrocarbyl radical, $R_2$ is hydrogen or the methyl group, and x is about 3–7. The thus prepared pillared interlayered clay exhibits high surface area, high methane storage capacity and high resolution in separating gaseous hydrocarbons.

22 Claims, No Drawings

PREPARATION OF PILLARED CLAY

BACKGROUND OF THE INVENTION

This invention relates to a process for preparing pillared interlayered clays. In another aspect, this invention relates to a process for preparing a pillared clay exhibiting enhanced surface area, enhanced gas storage capacity and improved selectivity in the separation of gases.

The preparation of pillared interlayered clay compositions by reacting a smectite-type clay with an aqueous solution of a suitable polymeric cationic hydroxy metal complex of a metal, such as aluminum, titanium, zirconium and chromium, is well known. Upon dehydration of the reaction product, there results a smectite clay which includes additional metal oxide, such as oxide of Al, Ti, Zr or Cr, in the form of pillars interspersed between the clay layers, as is illustrated in U.S. Pat. Nos. 4,637,991, 4,238,364, 4,216,188 and 4,176,090, herein incorporated by reference. These known clay products having interspersed pillars of metal oxide, such as oxide of Al, Ti, Zr or Cr, (said products being referred to hereinafter as pillared interlayered clays) exhibit advantages in various applications (such as catalytic cracking and gas separation) over untreated (unpillared) smectite clays. However, there is an ever present need to develop improved processes for preparing pillared interlayered clays, in particular processes resulting in pillared clays possessing enhanced surface area and gas storage capacity, and exhibiting enhanced selectivity in the separation of hydrocarbon gases.

SUMMARY OF THE INVENTION

It is an object of this invention to provide a process for preparing improved pillared interlayered clays. It is another object of this invention to provide pillared interlayered clays exhibiting increased surface area, enhanced gas storage capacity and improved selectivity in gas separation. Other objects and advantages will be apparent from the detailed description and the appended claims.

In accordance with this invention, in a process for preparing a pillared interlayered clay comprising the step of contacting a smectite clay containing material with a solution comprising at least one polymeric cationic hydroxy metal complex of at least one metal (i.e., one metal or a mixture of two or more metals) selected from the group consisting of aluminum, titanium, zirconium and chromium, under such contacting conditions as to increase the content of said metal in said smectite clay;

the improvement comprises the presence, during said contacting, of at least one surfactant having the general chemical formula of $R^1$—O—$(CHR^2$—$CHR^2O)_xH$, wherein $R^1$ is a linear or branched aliphatic hydrocarbyl group having from 6 to about 24 carbon atoms, $R^2$ is H or the methyl group, and x is a whole number in the range of 3 to 7.

In a preferred embodiment, a process for preparing a pillared interlayered clay comprises the steps of (a) contacting a smectite clay with an aqueous solution comprising (i) at least one polymeric cationic hydroxy metal complex of aluminum and (ii) at least one surfactant having the general chemical formula of $R^1$—O—$(CH_2$—$CH_2O)_xH$, wherein $R^1$ is a linear or branched aliphatic hydrocarbyl group having about 6 to about 24 carbon atoms, and x is a whole number in the range from about 3 to 7, wherein said contacting is carried out under such contacting conditions as to increase the aluminum content in said smectite clay;

(b) separating the smectite clay having increased aluminum content, obtained in step (a), from said aqueous solution used in step (a); and (c) heating the separated smectite clay having increased content of aluminum, obtained in step (b), under such heating conditions as to remove substantially all water from the separated smectite clay having increased content of aluminum, and to obtain a pillared interlayered clay.

Also in accordance with this invention, a pillared interlayered clay is provided having been prepared by a process comprising steps (a), (b) and (c), as outlined above. The thus prepared pillared interlayered clay possesses increased surface area (determined by the BET method employing $N_2$) and enhanced gas storage capacity (determined in accordance with the procedure described in Example II) and exhibits enhanced selectivity in separating methane from ethane and ethane from propane (determined in accordance with the procedure described in Example III of U.S. Pat. No. 4,637,991), as compared with a pillared interlayered clay which has been prepared by a process comprising steps (a), (b) and (c) in the absence of said surfactant in said solution used in step (a).

DETAILED DESCRIPTION OF THE INVENTION

The smectite clay containing starting material of the present invention generally comprises (preferably consist essentially of) a clay mineral commonly called smectite, as defined in U.S. Pat. Nos. 4,176,090 and 4,452,910, herein incorporated by reference. Non-limiting examples of suitable smectite clays are bentonite, montmorillonite, chlorite, vermiculite, nontronite, hectorite, saponite, beidellite and mixtures thereof, preferably bentonite. It is within the scope of this invention to use smectite clays which have been contacted with carboxylates, bicarbonates and carbonates as described in U.S. Pat. No. 4,742,022, the disclosure of which is herein incorporated by reference.

In the process for preparing interlayered clays in accordance with this invention, the smectite clay containing starting material (preferably a smectite clay) is contacted with a solution (preferably aqueous) comprising (i) at least one polymeric cationic hydroxy metal complex (sometimes also referred to as oligomer) of at least one of Al, Ti, Zr and Cr, as defined in U.S. Pat. Nos. 4,452,910, 4,238,364, 4,216,188 and 4,176,090, all herein incorporated by reference, and (ii) at least one surfactant having the general chemical formula of $R^1$—O—$(CHR^2$—$CHR^2O)_xH$, as defined above. Preferably, in particular in step (a), as defined above, the polymeric cationic hydroxy metal complex is a polymeric cationic hydroxy aluminum complex, as defined in several of the above-incorporated patents and also in U.S. Pat. No. 4,271,043, herein incorporated by reference. The preferred polymeric hydroxy aluminum complex is a polymeric hydroxy aluminum chloride, more preferably one contained in Chlorhydrol®, as described in Example I.

Generally the Chlorhydrol® solution is diluted with water. Preferably, the aqueous contacting solution contains from about 0.01 to about 10 weight-% (preferably about 0.1–3 weight-%) of polymeric aluminum hydroxy chloride. More preferably, the dissolved polymeric aluminum hydroxy chloride has been aged at a temperature in the range of about 20° C. to about 100° C. for a period of about 10 minutes to about 300 days, preferably at about 25°-70° C. for about 3 to 50 days, as has been described in U.S. Pat. No. 4,637,991. Generally, the weight ratio of polymeric aluminum hydroxy compound (preferably halide) to the smectite clay in step (a) is in the range of from about 0.001:1 to about 10:1, preferably from about 0.01:1 to about 1:1.

The surfactant (ii) can be used in any suitable concentration in said solution, preferably at a concentration of from about 0.01 to about 10 grams per liter solution, more preferably from about 0.1 to about 5 grams per liter. In the presently preferred surfactants, the $R^1$ radical contains about 12-15 carbon atoms and about 25-31 hydrogen atoms, $R^2$ is hydrogen, and x is about 4-6. Particularly preferred surfactants are described in Example I.

Any suitable contacting conditions and contacting means can be employed in step (a) resulting in an increased metal (preferably Al) content in the clay product. The contacting temperature generally is in the range of about 20° C. to about reflux temperature such as about 100° C. at about 1 atm., preferably from about 25 to about 80° C. The pressure in step (a) can be subatmospheric, atmospheric (about 1 atm; presently preferred) or superatmospheric. The contacting time in step (a) greatly depends on the reaction temperature, and generally is in the range of from about 1 minutes to about 10 hours, preferably from about 0.2 to about 2 hours. Preferably, step (a) is carried out in any suitable vessel with agitation and, optionally, under reflux conditions. Generally, the Al content in the clay product increases by about 0.1 to about 10 weight-%, based on the weight of the clay material that is treated in step (a).

Any separation technique can be used for carrying out separating step (b), such as filtration, centrifugation, settling and decanting of the supernatant solution, and the like. The presently preferred separation method in step (b) is filtration of the slurry obtained in step (a) so as to recover the solid clay product dispersed therein. The thus separated and recovered clay product having increased Al content is preferably further purified by washing with water (or a suitable aqueous solution) in any suitable manner, such as passing water through the filter cake or slurrying the filter cake in water and filtering again.

The separated clay product from step (b) is heated (calcined) in step (c) in any suitable gas atmosphere, preferably in air or another free oxygen containing gas mixture, under such conditions as to form a pillared interlayered clay. The calcination conditions comprise a temperature in the range of from about 200° to about 900° C. Preferably, the clay product from step (b) is first heated at a temperature in the range of from about 100° C. to about 200° C. so as to substantially dry the clay product (to less than about 50 weight-% $H_2O$). Thereafter, the substantially dried clay product is heated (calcined), preferably at a temperature in the range of from about 300° to about 700° C. (more preferably 500°-650° C.) and for a time period in the range of from about 0.1 to about 100 hours (preferably 1-10 hours). The heating (calcining) conditions of step (c) are such as to drive out a substantial portion of removable water. Preferably, the water content in the calcined pillared interlayered clay is less than about 5 weight-% of removable $H_2O$. In a preferred embodiment, steps (a) and (b) are repeated at least once, prior to calcining step (c), as has been described in Example III.

The pillared interlayered clay of this invention generally contains about 15-35 weight-% $Al_2O_3$, about 60-75 weight-% $SiO_2$ and about 1-5 weight-% Ca and/or Mg. The surface area of the pillared interlayered clay, as determined by the BET method (employing nitrogen, substantially in accordance with ASTM method D3037), can be in the range of from about 100 to about 500 $m^2/g$, preferably from about 200 to about 350 $m^2/g$. The pillared interlayered clay formed in step (c) can be ground to a smaller particle size and sieved.

The pillared interlayered clay obtained in step (c), having enhanced surface area (as determined by the BET method employing nitrogen) can be used as a catalyst or a catalyst support or a catalyst component in a variety of catalytic processes, such as hydrocracking of petroleum or petroleum fractions, isomerization, oligomerization, and the like. The pillared interlayered clay can be used as is; or it can be impregnated with a hydrogenated promoter, such as compounds of nickel and/or molybdenum, as has been described in U.S. Pat. No. 4,637,991; or it can be admixed with a zeolite so as to prepare an effective cracking catlyst, as has been described in U.S. Pat. No. 4,742,033; or it can be exchanged with ammonium or metal ions, as has been described in U.S. Pat. Nos. 4,742,033 and 4,637,991.

The pillared interlayered clay obtained in step (c), which possesses enhanced methane storage capacity and exhibits enhanced selectivity in separating methane from ethane and ethane from propane, can be used for separating components of gas mixtures, in particular the separation of components contained in natural gas, as has been described in U.S. Pat. No. 4,637,991. It is also feasible to employ the pillared interlayered clay of this invention for separating oxygen from nitrogen and hydrogen from nitrogen, as has been described in U.S. Pat. No. 4,637,991. Furthermore, the pillared interlayered clay of this invention can be used for storage of methane in steel tanks (described in Example II).

The following examples are present to further illustrate the invention and are not to be considered unduly limiting the scope of this invention.

EXAMPLE I

This example illustrates the preparation of several pillared interlayered bentonite clays.

Pillared Clay A (Control) was prepared substantially in accordance with the procedure of Example I in U.S. Pat. No. 4,637,991. A sample of 30 cc of Chlorhydrol ® (a 50 weight-% aqueous solution of an aluminum hydroxy chloride having the appropriate formula of $Al_2(OH)_5Cl\cdot 2H_2O$ and a molecular weight of about 210; provided by Reheis Chemical Company, Berkely Heights, NJ) was mixed with 2970 cc of distilled water. The thus-diluted Chlorhydrol ® solution was allowed to age at room temperature for about 2 weeks. Then 67 grams of bentonite clay (supplied by American Colloid Company, Skokie, Ill.) were added to the aged diluted Chlorhydrol solution. The obtained mixture of bentonite clay and diluted Chlorhydrol ® solution was stirred at 65° C. for 1 hour. After this pillaring treatment, the obtained slurry was filtered. The filter cake was reslurried in 1 liter of distilled water and stirred, followed by filtration, reslurrying in water as described above, and final filtration. The thus obtained washed filter cake was dried at about 100° C. for about 1 hour, and then calcined in air at about 500° C. for about 1 hours. The calcined pillared clay was ground and sieved. A portion of the sieved material having a particle size of less than 100 mesh was evaluated, as described in Example II.

Pillared Clay B (Invention) was prepared in accordance with the method for Pillared Clay A except that 3 g of Tergitol 25-L-5 was present in the diluted Chlorhydrol ® solution during pillaring. Tergitol ® 25-L-5 was an ethoxylated primary alcohol (also referred to as polyethylene glycol monoether or a primary alcohol). Tergitol 25-L-5 had an approximate chemical formula of $C_{12-15}H_{25-31}O(CH_2CH_2O)_5H$, an average molecular weight of about 440, and a specific gravity of 0.955; and was provided by Union Carbide Corporation, Danbury, CT.

Pillared Clay C (Invention) was prepared in accordance with the procedure for Pillared Clay A except that 3.0 g Tergitol 15-S-5 was present in the diluted Chlorhydrol ® solution during pillaring. Tergitol 15-S-5 was an ethyoxylated secondary alcohol (also referred to as polyethylene glycol monoether of a secondary alcohol). Tergitol 15-S-5 had an approximate chemical formula of $C_{12-14}H_{25-29}O(CH_2CH_2O)_5H$, an average molecular weight of about 420, and a specific gravity of 0.965; and was provided by Union Carbide Corporation.

Pillared Clay D (Control) was prepared in accordance with the procedure for Pillared Clay A except that 3.0 g Tergitol 15-S-40, another ethoxylated secondary alcohol, was present in the diluted Chlorhydrol ® solution during pillaring. Tergitol 15-S-40 had an approximate chemical formula of $C_{11-15}H_{23-31}O(CH_2CH_2O)_{40}H$, an average molecular weight of about 1960, and a specific gravity of 1.066; and was provided by Union Carbide Corporation.

Pillared Clay E (Control) was prepared in accordance with the procedure for Pillared Clay A except that 3.0 g of Trycol NP407 was present in the diluted Chlorhydrol ® solution during pillaring. Trycol NP 407 was an ethoxylated nonylphenol (provided by Union Carbide) having an approximate formula of $C_9H_{19}C_6H_4O(CH_2CH_2O)_{40}H$, an average molecular weight of about 1980, and a specific gravity of 1.080.

Pillared Clay F (Invention) was prepared in accordance with the procedure for Pillared Clay A except that 1.1 g Tergitol 25-L-5 and additionally 0.4 g of Witco TRS 10–410 were present in the diluted Chlorhydrol ® solution during pillaring. Witco TRS 10–410 was an ionic surfactant of the general formula $R-C_6H_4-SO_3Na$, provided by Witco Corporation, New York, NY.

EXAMPLE II

This example illustrates the effects of specific methods of preparing pillared clays on surface area (determined by BET absorption method employing $N_2$), methane storage capacity, the separation of methane/ethane and the separation of ethane/propane.

The methane storage capacity (i.e., a measure of methane capable of being held under a specific pressure in a steel tank filled with pillared clay beyond that an empty steel tank would hold under the same pressure) was determined as follows. First, an empty 33 cc steel bomb was evacuated by means of a pump, and weighed (=weight $W_1$). Then the empty steel bomb was pressured with 200 psig $CH_4$ and weighed again (=weight $W_2$). In a separate test, the bomb was opened, filled with 25 cc pillared clay, evacuated, and weighed (=weight $W_3$). Then the bomb containing 25 cc of pillared clay was pressured with 200 psig $CH_4$, and weighed again (=weight $W_4$). The methane storage capacity (in mg $CH_4$ per g pillared clay) was calculated as follows:

$$\frac{(W_4 - W_3) - (W_2 - W_1)}{W_3 - W_1} \times 1000.$$

The effectiveness of the pillared clays for separating methane from ethane and ethane from propane was quantitatively expressed by the resolution R which was determined in accordance with the procedure for separating components in a natural gas, described in Example III of U.S. Pat. No. 4,637,991. Test results are summarized in Table I.

TABLE I

| Pillared Clay | Surface Area ($m^2/g$) | Resolution R | | Methane Storage Capacity (mg/g)* |
|---|---|---|---|---|
| | | $C_1/C_2$ | $C_2/C_3$ | |
| A (Control) | 182 | 4.4 | 4.3 | 0.9 |
| B (Invention) | 251 | 8.7 | 7.5 | 3.7 |
| C (Invention) | 278 | 7.6 | 5.1 | 5.4 |
| D (Control) | 148 | 3.6 | 2.9 | 1.0 |
| E (Control) | 162 | 3.2 | 2.8 | 0.7 |
| F (Invention) | 277 | 8.3 | 5.8 | 1.4 |

*mg methane per g pillared clay.

Test data in Table I clearly show the advantages (higher surface area, better gas separation and greater methane storage capacity) of invention Pillared Clays B, C and F, which were prepared in the presence of a polyethoxylated alcohol having about five ethoxy groups (Tergitol 25-L-5 and 15-S-5) over Pillared Clay A, which was prepared in the absence of a surfactant, and over Pillared Clays D and E, which were prepared in the presence of polyethoxylated alcohols having about 40 ethoxy groups (Tergitol 15-S-40 and Trycol NP407).

EXAMPLE III

This example illustrates the effect of multiple (repeated) pillaring, in the presence of Tergitol 25-L-5, the polyethoxylated alcohol having about 5 ethoxy groups, described in Example I.

Pillared Clay G (Invention) was prepared in accordance with the procedure for Pillared Clay B, except that the pillaring of Bentonite clay at 65° C. was carried out for 4 hours (instead of only 1 hour) so as to obtain Intermediate Pillared Clay G; and the pillaring process at 65° C. was repeated for 2 hours with the washed filter cake of Intermediate Pillared Clay G, so as to obtain Pillared Clay G, which was thereafter dried and calcined in accordance with the procedure described for Pillared Clay A.

Pillared Clay H (Invention) was prepared substantially in accordance with the procedure for Pillared Clay B, except that the treatment of Bentonite Clay at 65° C. carried out with the diluted Chlorhydrol ® solution for 2 hours (rather than 1 hour), so as to obtain First Intermediate Pillared Clay H1; and the pillaring process was repeated twice. First Intermediate Pillared Clay H1 was dried and treated with the above pillaring solution at 65° C. for 2 hours, separated from the pillaring solution by filtration, washed and dried so as to obtain Second Intermediate Pillared Clay H2. Finally, dried Second Intermediate Pillared Clay H2 was treated with the pillaring solution of 65° C. for 2 hours, separated, washed, dried and calcined (in accordance with the procedure described for Pillared Clay A), so as to obtain Pillared Clay H.

Pillared Clays G and H were tested for surface area, methane absorption, separation of methane from ethane and separation of ethane from propane, in accordance with the procedures described in Example II. Test results are summarized in Table II.

TABLE II

| Pillared Clay | Surface (Area (m²/g) | Methane Storage Capacity (mg/g) | Resolution $C_1/C_2$ | $C_2/C_3$ |
|---|---|---|---|---|
| B (pillared once) | 251 | 3.7 | 8.7 | 7.5 |
| G (pillared twice) | 228 | 4.1 | 13.1 | 10.8 |
| H (pillared thrice) | 240 | 1.3 | 11.0 | 8.7 |

Test results in Table II indicate that multiple pillaring had a beneficial effect on the effectiveness in separating methane from ethane and ethane from propane. However, pillaring more than twice did not result in additional benefits versus those attained by double pillaring.

Reasonable variations and modifications which will be apparent to those skilled in the art, can be made within the scope of the disclosure and appended claims without departing from the scope of this invention.

That which is claimed is:

1. In a process for preparing a pillared interlayered clay comprising the step of contacting a smectite clay containing material with a solution comprising at least one polymeric cationic hydroxy metal complex of at least one metal selected from the group consisting of aluminum, titanium, zirconium and chromium, under such contacting conditions as to increase the content of said at least one metal in said smectite clay;
the improvement which comprises the presence, during said contacting, of at least one surfactant having the general chemical formula of $R^1$—O—($CHR^2$—$CHR^2O$)$_x$H, wherein $R^1$ is an aliphatic hydrocarbyl group having from 6 to about 24 carbon atoms, $R^2$ is H or the methyl group, and $x$ is a whole number in the range of 3 to 7.

2. A process in accordance with claim 1, wherein said at least one metal is aluminum.

3. A process in accordance with claim 1, wherein $R^1$ contains about 12–15 carbon atoms, $R^2$ is hydrogen, and $x$ is about 4–6.

4. A process in accordance with claim 1, wherein said smectite clay containing material consists initially of bentonite.

5. A process for preparing a pillared interlayered clay comprising the steps of
(a) contacting a smectite clay with an aqueous solution comprising (i) at least one polymeric cationic hydroxy metal complex of aluminum and (ii) at least one surfactant having the general chemical formula of $R^1$—O—($CH_2$—$CH_2O$)$_x$H, wherein $R^1$ is an aliphatic hydrocarbyl group having about 6 to about 24 carbon atoms, and $x$ is a whole number in the range from about 3 to 7, wherein said contacting is carried out under such contacting conditions as to increase the aluminum content in said smectite clay;
(b) separating the smectite clay having increased aluminum content obtained in step (a) from said aqueous solution used in step (a); and
(c) heating the separated smectite clay having increased content of aluminum, obtained in step (b) under said heating conditions as to remove substantially all water from said smectite clay having increased content of aluminum, and to obtain a pillared interlayered clay.

6. A process in accordance with claim 5, wherein $R^1$ contains about 12–15 carbon atoms and $x$ is about 4–6.

7. A process in accordance with claim 5, wherein said smectite clay used in step (a) is bentonite.

8. A process in accordance with claim 5, wherein said polymeric cationic hydroxy metal complex of aluminum is polymeric aluminum hydroxy chloride.

9. A process in accordance with claim 5, wherein said aqueous solution used in step (a) contains about 0.01 to about 10 weight-% of said polymeric cationic hydroxy complex of aluminum, and about 0.01 to about 10 g/l of said surfactant.

10. A process in accordance with claim 5, wherein said polymeric cationic hydroxy complex of aluminum is a dissolved polymeric aluminum hydroxy chloride which has been aged at a temperature in the range of about 20° to about 100° C. for a time period in the range of about 10 minutes to about 300 days.

11. A process in accordance with claim 5, wherein the weight ratio of said polymeric aluminum hydroxy compound to said smectite clay in step (a) is in the range of from about 0.001:1 to about 10:1, and said contacting conditions in step (a) comprise a temperature in the range of about 20° to about 100° C. and a contacting time of about 1 minute to about 10 hours.

12. A process in accordance with claim 5, wherein said heating in step (c) is carried out at a temperature in the range of about 200° to about 900° C., and wherein the surface area of said pillared interlayered clay, as determined by the BET method employing nitrogen, is in the range of about 100 to about 500 m²/g.

13. A process in accordance with claim 5, wherein steps (a) and (b) are repeated at least once, before step (c) is carried out.

14. A pillared interlayered clay having been prepared by a process comprising the steps of
(a) contacting a smectite clay with an aqueous solution comprising (i) at least one polymeric cationic hydroxy metal complex of aluminum and (ii) at least one surfactant having the general chemical formula of $R^1$—O—($CH_2$—$CH_2O$)$_x$H, wherein $R^1$ is an aliphatic hydrocarbyl group having about 6 to about 24 carbon atoms, and $x$ is a whole number in the range from about 3 to 7, wherein said contacting is carried out under such contacting conditions as to increase the aluminum content in said smectite clay;
(b) separating the smectite clay having increased aluminum content obtained in step (a) from said aqueous solution used in step (a); and
(c) heating said smectite clay having increased content of aluminum, obtained in step (b), under such heating conditions as to remove substantially all water from said smectite clay material having increased content of aluminum, and to obtain a pillared interlayered clay.

15. A pillared interlayered clay in accordance with claim 14, wherein $R^1$ contains about 12–15 carbon atoms and $x$ is about 4–6.

16. A pillared interlayered clay in accordance with claim 14, wherein said smectite used in step (a) is bentonite.

17. A pillared interlayered clay in accordance with claim 14, wherein said polymeric cationic hydroxy metal complex of aluminum is polymeric aluminum hydroxy chloride.

18. A pillared interlayered clay in accordance with claim 14, wherein said aqueous solution used in step (a) contains about 0.01 to about 10 weight-% of said polymeric cationic hydroxy complex of aluminum, and about 0.01 to about 10 g/l of said surfactant.

19. A pillared interlayered clay in accordance with claim 14, wherein said polymeric cationic hydroxy complex of aluminum is a dissolved polymeric aluminum hydroxy chloride which has been aged at a temperature of about 20 to about 100° C. for a time period of about 10 minutes to about 300 days.

20. A pillared interlayered clay in accordance with claim 14, wherein the weight ratio of said polymeric aluminum hydroxy compound to said smectite clay in step (a) is in the range of about 0.001:1 to about 10:1, and said contacting conditions in step (a) comprise a temperature in the range of about 20° to about 100° C. and a contacting time of about 1 minute to about 10 hours.

21. A pillared interlayered clay in accordance with claim 14, wherein said heating in step (c) is carried out at a temperature in the range of about 200° to about 900° C., and wherein the surface area of the pillared interlayered clay, as determined by the BET method employing nitrogen, is in the range of about 100 to about 500 m²/g.

22. A pillared clay in accordance with claim 14, wherein steps (a) and (b) are repeated at least once, before step (c) is carried out.

* * * * *